United States Patent [19]

Meilland

[11] Plant 5,046

[45] May 3, 1983

[54] ROSE PLANT—MEIRANDIVAL VARIETY

[75] Inventor: Marie L. Meilland, Antibes, France

[73] Assignee: The Conard-Pyle Company, West Grove, Pa.

[21] Appl. No.: 130,753

[22] Filed: Mar. 17, 1980

[30] Foreign Application Priority Data

Apr. 3, 1979 [NL] Netherlands ..... ROO 1000

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which has double bicolored flowers and vigorous vegetation. The petals are yellowish-white in color suffused with geranium lacquer on the edges. The new variety is a sport of the Meibiranda variety which is described in U.S. Pat. Ser. No. 76,311, filed Sept. 17, 1979.

15 Drawing Figures

SUMMARY OF THE INVENTION

The object of the present invention is to provide a new variety of rose plant of the Hybrid Tea Class having double distinctively colored flowers.

The new variety was discovered while growing in a cultivated area among plants of the Meibiranda variety. It is considered to be a sport or mutation of such Meibiranda variety which is described in U.S. Ser. No. 76,311, filed Sept. 17, 1979. The characteristics of the new variety substantially correspond to those of the Meibiranda variety with the exception that the double bicolored flowers of the new variety are yellowish-white in color suffused with geranium lacquer on the edges. On the contrary the double bicolored flowers of the Meibiranda variety are mimosa yellow in color with poppy red on the edges. The flowers of each variety are of substantially the same shape.

Extensive testing of many plants has confirmed the behavior and productivity of the new variety. The results were conclusive and have documented the creation of an important new rose variety suitable for commercial exploitation by commercial nurserymen and producers of cut flowers.

The characteristics and properties of this new variety are strictly transmissible by agamic means, also called "asexual", i.e. by means of vegetative propagation, in particular by grafting an eye. The rose plant of the new variety has been designated the Meirandival variety.

BRIEF DESCRIPTION OF THE PHOTOGRAPH

The accompanying photograph shows as nearly true as it is reasonably possible to make the same in a color illustration of this character, typical specimens of the cut flowers, foliage and other elements of the new variety, illustrated in:

FIG. 1 — a specimen of a young shoot;

FIG. 2 — a specimen of a bud before the sepals burst open;

FIG. 3 — a specimen of a bud at the opening of the sepals;

FIG. 4 — a specimen of a bud at the first opening of the petals;

FIG. 5 — a specimen of a flower in the course of opening;

FIG. 6 — a specimen of an open flower, plan view, obverse;

FIG. 7 — a specimen of an open flower, plan view, reverse;

FIG. 8 — a specimen of a fully open flower, plan view, obverse;

FIG. 9 — a specimen of a floral receptacle showing the arrangement of the stamens (sepals removed);

FIG. 10 — a specimen of a floral receptacle showing the arrangement of the pistils (sepals and stamens removed);

FIG. 11 — a portion of floral stem;

FIG. 12 — a portion of a main branch;

FIG. 13 — a specimen of a 3-foliole leaf — upper surface;

FIG. 14 — a specimen of a 7-foliole leaf — upper surface; and

FIG. 15 — a specimen of a 5-foliole leaf — under surface.

DETAILED DESCRIPTION OF THE DISCLOSURE

The plants described herein were grown under glass in Holland.

The chart used in the identification of the colors is that of The Royal Horticultural Society (R.H.S. Colour Chart). The terminology preceding the numbered references proper to this chart has been added to designate, in common terms, the corresponding colors.

Class: Hybrid tea.

Plant:

*Height.*—1.25 to 1.45 meters. Stems commonly can be cut in greenhouses which are 40 to 60 centimeters in length.

*Habit.*—Straight.

Branches:

*Color.*—Young stems: bronze green 146/A (yellow green group) very slightly shaded reddish. Mature wood: bronze green 146/A (yellow green group).

*Thorns.*—Shape: Upper edge: straight shape, tapered, slightly inflected towards the base. Under edge: concave. Size: medium. Quantity: fairly numerous, sometimes intermingled with small aciculae. Color: On young stems: reddish. On mature wood: straw, then Havana brown (common terms).

Leaves:

*Stipules.*—Adnate, pectinate, fairly wide and linear.

*Petioles.*—Inner surface: grooved, reddish brown (young leaves), medium green (mature leaves), more or less glandular edges. Outer surface: light green, bears a few small hooked and acicular thorns.

*Folioles.*—Number: 3 to 5 most frequently, also 7. Shape: oval, with rounded base. Teeth: simple and regular. Texture: leathery. General effect: ample foliage, moderately dense and semi-dull in appearance. Color: Young foliage: Upper surface: dark green 147/A (Yellow green group) more or less shaded reddish. Under surface: bronze green 148/B (Yellow green group) more or less shaded reddish. Adult foliage: Upper surface: dark green 147/A (yellow green group). Under surface: medium green 147/B (yellow green group).

Inflorescense:

*Number of flowers.*—Generally one flower per stem.

*Peduncle.*—Straight, rigid, sometimes very slightly spotted reddish brown, it bears a fair number of little hooked prickles. Length: 9 to 11 centimeters on average.

*Sepals.*—Upper surface: tomentous, greenish. Under surface: light green, more or less glandular, with top more or less spotted reddish. The outer sepals have their edges very largely appendiculate. Fairly often one of them diversifies itself into an embryo of a leaflet.

*Bud.*—Shape: before the opening of the sepals it is conical. Length: 36 millimeters on the average outside the calyx at the opening of the sepals. Size: fairly bulky. Color: On opening: Upper surface: pale yellow suffused with mottled red 39/A (red group) on the edges. Under surface: yellowish white suffused with mottled red 39/A (red group) on the edges.

*Flower.*—Form: first of all cup shaped with parallel sides, petals well imbricated, then it opens to a hollow cup shape form when fully open; double flower. Diameter: 12 to 13 centimeters. Color: When first opening: Upper surface: yellowish-white more or less suffused with geranium lacquer 47/D (red group), increasing on the edges. Under surface: yellowish-white bordered with a thin suffusion of geranium lacquer — 47/D (red group). During the course of opening: Upper surface: yellowish-white more or less suffused with geranium lacquer 47/D (red group) on the edges. Under surface: yellowish-white bordered with a thin suffusion of geranium lacquer 47/D (red group). When fully open: Upper surface: yellowish-white more or less suffused with empire pink 48/C (red group) on the edges. Under surface: yellowish-white, bordered with a thin suffusion of empire pink 48/C (red group). Fragrance: none. Lasting quality: long. Corolla: Petals: Texture: firm. Shape: rounded, with sides folded back. The unguis is small and yellow on both surfaces. Number: 25 on an average, 2 or 3 petals commonly not whole in the center. Stripping: the petals drop off cleanly. Stamens: Number: 64 on an average. Anthers: ochered at terminal insertion. Filaments: yellow, irregular in height. Pistils: Number: 60 on average. Stigmas: normal, straw yellow. Styles: free, straw — greenish, slightly twisted and tomentous. Receptacle: light green, at the dehiscence of the anthers and in longitudinal cross-section it is narrow and in the shape of a funnel.

Development:

*Vegetation.*—Vigorous.

*Flowering.*—Nearly continuous under glass.

*Resistance to diseases.*—Good.

I claim:

1. A new and distinct variety of Hybrid Tea rose plant of vegetative reproduction, substantially as illustrated and described, characterized by the fact that:

from the physical point of view the plant with bronze green adult wood is erect, forms double flowers which are yellowish-white in color suffused with geranium lacquer on the edges, and forms petals which bear a yellow unguis on both surfaces; and from the biological point of view the plant has vigorous vegetation, exhibits nearly continuous flowering under glass, and forms flowers of long duration both on and off the plant.

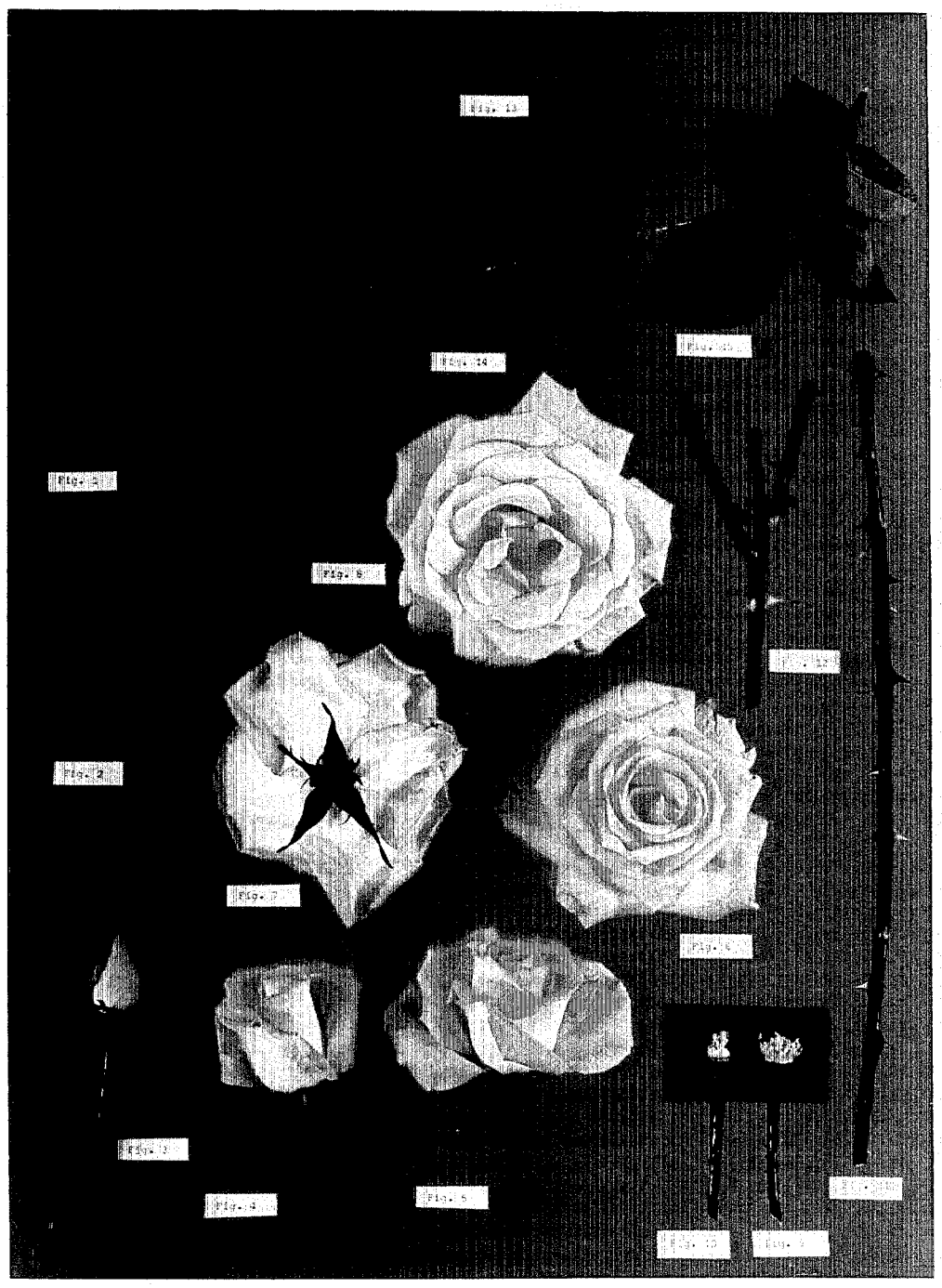

* * * * *